United States Patent [19]

Gardner et al.

[11] 4,178,466

[45] Dec. 11, 1979

[54] PROCESS FOR PREPARING PHENYL TRICHLORO-ETHANES

[75] Inventors: Russell A. Gardner, Voorheesville; Charles M. Orlando, Scotia, both of N.Y.

[73] Assignee: General Electric Company, Schenectady, N.Y.

[21] Appl. No.: 886,727

[22] Filed: Mar. 15, 1978

[51] Int. Cl.$^2$ ............................................. C07C 39/16
[52] U.S. Cl. ...................................................... 568/727
[58] Field of Search ................................ 568/726, 727

[56] References Cited

U.S. PATENT DOCUMENTS

| | | | |
|---|---|---|---|
| 2,766,293 | 10/1956 | Miville et al. | 568/726 |
| 2,822,404 | 2/1958 | Ambelang | 568/727 |

FOREIGN PATENT DOCUMENTS 1189499 4/1970 United Kingdom ................. 568/726

OTHER PUBLICATIONS

Ter Meer "Ber." vol. 7 (1874), pp. 1201-1202.
Auwers "Ber." vol. 36, pp. 1878 (1889).
Frankforter et al., "J. Amer. Chem. Soc.", vol. 36 (1914), 1520-1523.
Zaheer et al., "J. Chem. Soc.", London (1955), pp. 1706-1709.

*Primary Examiner*—Werren B. Lone
*Attorney, Agent, or Firm*—Joseph T. Cohen; Leo I. MaLossi

[57] ABSTRACT

Phenyl trichloro-ethanes can be prepared by reacting chloral with a phenol compound, such as phenol itself or 2,6-xylenol in HF, which acts both as a catalyst and solvent medium.

6 Claims, No Drawings

PROCESS FOR PREPARING PHENYL TRICHLORO-ETHANES

This invention relates to a process for making a certain class of phenyl trichloro-ethanes. More particularly, the invention is concerned with a process for making a trichloro-ethane corresponding to the general formula

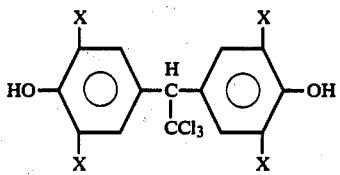

I which comprises reacting under condensation conditions a phenol compound of the general formula

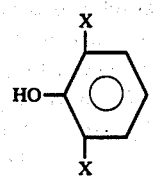

II and chloral in liquid HF and thereafter isolating the aforesaid trichloro-ethane, where X is the same or different members selected from the class consisting of hydrogen, the methyl radical, and halogens. Of particular interest is the preparation of the trichloro-ethane corresponding to the formula

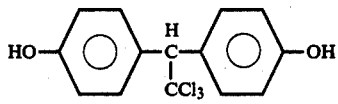

III from the reaction of phenol and chloral.

Among the phenol compounds of formula II which may be employed in the practice of the invention are included, for instance, phenol itself, 2,6-xylenol, ortho-cresol, 2,6-dichlorophenol, 2,6-dibromophenol, 2-chlorophenol, 2-bromophenol, 2-fluorophenol, 2-chloro-6-methylphenol, etc.

Phenol and chloral have been reacted in a variety of acidic media to provide a variable product composition of 2,2-bis(4-hydroxyphenyl)-1,1,1-trichloro-ethane (hereinafter identified as "p,p-trichloro compound") and 2-(4-hydroxyphenyl)-2(2-hydroxyphenyl)-1,1,1-trichloro-ethane (hereinafter identified as "o,p-trichloro compound"). Although the p,p-trichloro compound is the major product in these reactions, it is often accompanied by from 8 to 20% or more of the o,p-trichloro compound depending on the acidic medium and reaction conditions. For instance, diphenyl trichloro-ethanes, such as the aforesaid p,p-trichloro isomer, have in the past been prepared by the condensation of phenol and chloral in a solvent medium comprising sulfuric acid and acetic acid. [See E. TerMeer, *Ber.*, 7, 1201 (1874); E. Von Auwers, *Ber.*, 36, 1878 (1889).] While the crude product obtained by this method may be in an acceptable yield, it is often highly colored and contaminated with substantial quantities of by-products, notably the aforementioned o,p-trichloro compound. In addition to the above disadvantages, careful temperature control is needed to avoid sulfonation of the unreacted phenol. The acetic acid, although acting to moderate the acidity, nevertheless, significantly adds to the cost of the process. Moreover, because of the high heat of solution between the concentrated sulfuric acid and the acetic acid/phenol mixture, it is still necessary to introduce highly sophisticated cooling means, which again adds to the cost of the process.

One of the more sought-after attributes of a process is to be able to carry out the process on a continuous basis. This usually means that at some stage in the process, the reaction product should be capable of being readily removed and the process is capable of recycling either unused portions of the initial reactants or else to refurbish depleted reactants to bring them up to a level where they can be used again on a continuous basis in making more of the desired reaction product. The use of acetic acid as a cosolvent makes it difficult to carry out a recycle step in making the compound of formula III, for example.

We have now unexpectedly discovered that by using liquid HF in place of previous acidic media, one can effect reaction between a phenol of formula II and chloral without the necessity of using acetic acid as a cosolvent with its attendant disadvantages. We have also found that by using the low temperatures associated with the HF, cooling means normally employed when sulfuric acid and acetic acid are employed together, are now required only under minimal circumstances. By using the liquid HF, exceptionally good yields of desired product are realized with minimal quantities of the o,p-trichloro compound; at the same time, color is often better at any stage of the process and little purification processing is required.

The use of liquid hydrogen fluoride as the condensation catalyst and medium in the reaction between the phenol of formula II and the chloral eliminates the need for a large excess of phenol, pressure equipment, or elevated temperatures all normally required when using other acidic catalyzed reaction media. The hydrogen fluoride in addition to serving as a catalyst also serves as a solvent and is a very efficient catalyst in this reaction even at temperatures as low as $-30°$ C. The minimal levels of by-products and excess phenol compound in the reaction using the liquid HF enables a simple high-yield isolation of the p,p-trichloro compound derivative of formula I.

To find that the HF would work in connection with the reaction of chloral with the selected group of phenols itemized above to yield products in good yield and purity was entirely unexpected and in no way could have been predicted. When, for instance, acetone or cyclohexanone was substituted for the chloral, and reacted with, for example, either phenol or 2,6-xylenol, in the presence of the HF, degradation took place extensively and the yield of the desired dihydroxy diphenyl product was extremely low, e.g., from about 10 to 15%. Even the reaction of compounds which might be expected to resist the degradative effects of the HF, such as dimethoxypropane, paraformaldehyde, or dichloroacetaldehyde, when reacted with phenol or 2,6-xylenol, resulted in considerable degradation and low yields (and in some instances no yield) of between 2 to 25% of the desired product. In cases where paraformaldehyde was used, polymerization of the latter with phenol often accompanied low yields of the desired product.

As still further evidence of the unexpected and unobvious ability to use the HF in our invention, when strong fluorinated acids, such as trifluoroacetic acid, a mixture of trifluoroacetic acid and boron trifluoro etherate, and trifluoromethanesulfonic acid, were employed in the reaction of chloral and phenol, again extremely low yields of the desired trichloro-ethane were realized and the amount of the o,p-trichloro compound was quite high compared to the amount of the latter compound obtained when using the anhydrous HF.

The temperature at which reaction is carried out between the chloral and the phenol compound of formula II is usually well below that normally employed for reactions of this type. Thus, we have found that temperatures ranging from about 20° C. down to as low as −50° C. can be used, with the hydrogen fluoride still maintaining its activity as an extremely efficient catalyst. Generally temperatures of about 10° to −15° C. or lower are advantageously employed.

The ratio of the HF to the other ingredients can be varied widely and is not critical. By using the HF, advantage can be taken of being able to employ smaller quantities of the phenol compound than is normally used with the chloral. On a weight basis, one can employ from about 1 to 10 or more parts of the HF per part of phenol compound, and preferably from 2 to 6 parts, per part phenol.

The amount of phenol compound of formula II used can also be varied widely and is advantageously equal to at least 2 mols of the phenol compound per mol of the chloral, and generally within the range of from about 2 to 6 or more mols of the phenol compound per mol of chloral, and preferably from 2 to 3 mols of the phenol compound per mol chloral.

Inert and anhydrous atmospheres advantageously are employed throughout the reaction. This may be accomplished by employing a nitrogen blanket or other inert gas above the surface of the reaction mixture and by using well-known techniques for maintaining the HF and the reaction mixture as anhydrous as possible.

In carrying out the reaction, the phenol compound of formula II is conveniently first dissolved in the liquid HF, which has been cooled to low temperatures, such as about 0° to −30° C. Thereafter, the chloral is added slowly and the mixture stirred for times ranging from about 10 minutes to about 3 hours or more until the condensation reaction is completed. Thereafter the HF can be allowed to volatilize (and recycled if desired); any remaining HF in the reaction mixture is neutralized by quenching the latter by pouring it into cold water and then treatment with an alkali-metal compound, such as sodium bicarbonate or sodium hydroxide. The solids product which comprises mainly the p,p-trichloro compound of formula I is isolated by filtration, and the product dried. This will normally yield a p,p-trichloro compound of formula I of extremely high purity in yields of around 90% or higher.

Although the reaction proceeds quite satisfactorily at ambient (atmospheric) pressures, it will of course be understood by those skilled in the art that superatmospheric pressures may be employed without departing from the scope of the invention, provided excessively high temperatures (e.g., above 20° C.) are avoided in order to repress formation of the o,p-trichloro compound. Usually this is unnecessary because the reaction rate and product attainment at the reduced temperatures referred to above are more than satisfactory.

In order that those skilled in the art may better understand how the present invention may be practiced, the following examples are given by way of illustration and not by way of limitation. To maintain the temperature of reaction in the following examples below room temperature, cooling means were resorted to.

EXAMPLE 1

Into a 50 ml polypropylene cylinder (required to contain the HF) containing 3.7 grams phenol (0.04 mol) and a stirrer was added 10 ml liquid hydrogen fluoride. The temperature in the reaction vessel was stabilized at around −10° C., and thereafter 2.94 grams (0.02 mol) chloral was added dropwise. After stirring the reaction mixture for about 1 hour at around −10° C., the reaction mixture was quenched by pouring it into cold water. The acid solution which was obtained was neutralized with sodium bicarbonate and the solid crystallized product (which was essentially pure p,p-trichloro compound of formula III) was collected by filtration. The aqueous filtrate was then extracted with diethylether, dried and evaporated to a solid giving a combined weight of the p,p-trichloro compound of about 96% conversion. The combined solids were then dissolved in a minimum of methanol followed by silylation with bis(trimethylsilyl) acetamide in the manner described by Klebe et al in J.A.C.S. 88, 3390 (1966) and then analyzed by vapor phase chromatography using a 6'×⅛" Se-30 column with a temperature program of 150° to 300° C. at 10° C. per minute. VPC retention times for the o,p-trichloro compound and the p,p-trichloro compound are 12.0 and 13.0 minutes respectively. These tests showed that of the product 96.3% was the p,p-trichloro compound of formula III, and 3.7% was the o,p-trichloro compound.

EXAMPLE 2

In this example, chloral was condensed in the presence of HF with 2,6-xylenol in place of phenol using essentially the same conditions and molar proportions as employed in Example 1 to give almost a 100% yield of the trichloro-ethane compound having the formula

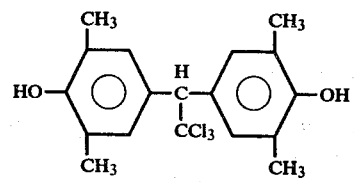

EXAMPLE 3

When 2,6-dibromophenol or 2,6-dichlorophenol is substituted for the phenol in Example 1 and reaction with chloral carried out in the presence of HF, using essentially the same conditions, procedures, and molar ratios as recited in Example 1, one obtains in good yields the phenyl trichloroethanes, respectively, having the formulas

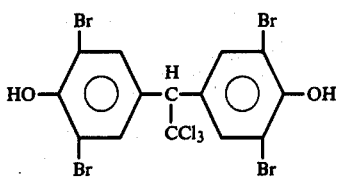

and

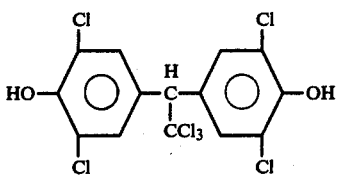

EXAMPLE 4

When ortho-cresol is substituted for the phenol in Example 1 and the reaction with chloral carried out in HF in the same manner as described in Example 1, one will obtain in good yield the phenyl trichloro-ethane having the formula

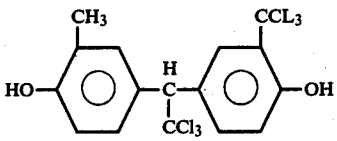

It will of course be understood by those skilled in the art that other conditions of reactions and ratios of reactants and ingredients as well as amounts of HF can be employed, many examples of which have been given above without departing from the scope of the invention. In addition, mixtures of phenol compounds of formula II can be reacted with the chloral in the presence of the HF to give mixed phenyl trichloro-ethanes. For example, phenol, 2,6-dibromophenol and chloral can be reacted simultaneously in the presence of HF to form a mixed phenyl trichloro-ethane, for instance, that having the formula

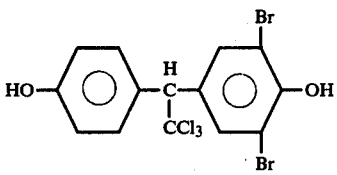

Persons skilled in the art will have no difficulty in ascertaining the actual conditions required for obtaining maximum yields and highest purity, taking into account the effects of the varying ratios of the phenol compound, the chloral, and the HF.

The compositions of matter obtained in accordance with the practice of the present invention have many uses. Thus, the dihydroxy diphenyl trichloro-ethanes of formula I can be used as precursor intermediates for making the monomer compositions (by dehydrohalogenation) having the general formula

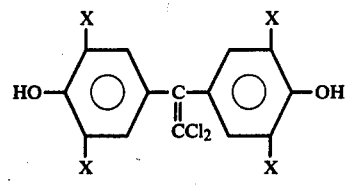

where X has the meaning above. The latter dichloroethylene compounds can be treated with a phosgenating agent such as phosgene, diphenyl carbonate, etc., to make polycarbonate resins which are useful in the preparation of flame-retardant and fire-resistant molded products such as housings for calculators, grills and dashboards for automobiles, etc.

What we claim as new and desire to secure by Letters Patent of the United States is:

1. The process for preparing a trichloro-ethane of the formula

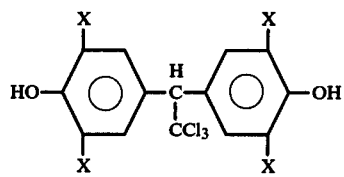

which comprises reacting at a temperature of from −50° to 20° C. a phenol of the formula

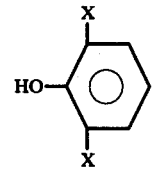

and chloral in liquid HF wherein the latter serves as both solvent and as catalyst for the reaction, and thereafter isolating the aforesaid trichloro-ethane, where X is the same or different member selected from the class consisting of hydrogen, the methyl radical and halogens.

2. The process as in claim 1 wherein the phenol is 2,6-xylenol.
3. The process as in claim 1 wherein the phenol is 2,6-dibromophenol.
4. The process as in claim 1 wherein the phenol is 2,6-dichlorophenol.
5. The process as in claim 1 whereby the phenol compound is first dissolved in the liquid HF prior to addition of the chloral.
6. The process for preparing a trichloro-ethane of the formula

III

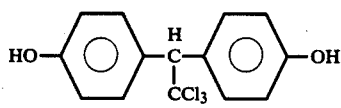

which comprises reacting at a temperature from −50° to 20° C. phenol with chloral in liquid HF wherein the latter serves as both a catalyst and a solvent, and thereafter isolating the aforesaid trichloro-ethane.

* * * * *